United States Patent [19]
Omoto et al.

[11] Patent Number: 5,183,742
[45] Date of Patent: Feb. 2, 1993

[54] TEST DEVICE FOR DETECTING GLUCOSE, PROTEIN UROBILINOGEN, AND/OR OCCULT BLOOD IN BODY FLUIDS AND/OR DETERMINING THE PH THEREOF

[75] Inventors: Kouichi Omoto, Kawasaki; Takeshi Miyazaki, Tokyo, both of Japan

[73] Assignee: Dai Nippon Insatsu Kabushiki Kaisha, Japan

[21] Appl. No.: 349,950

[22] Filed: May 8, 1989

Related U.S. Application Data

[63] Continuation of Ser. No. 703,480, Feb. 20, 1985, abandoned.

[30] Foreign Application Priority Data

Feb. 24, 1984 [JP] Japan .................. 59-33787

[51] Int. Cl.$^5$ .............................................. C12Q 1/54
[52] U.S. Cl. ............................................ 435/14; 435/23; 435/25; 435/28; 435/805; 436/86; 436/136; 436/163; 436/168; 436/170; 436/826; 422/56; 422/57; 422/58
[58] Field of Search .................. 422/56, 55, 57, 58; 436/136, 826, 168, 170, 86, 163; 435/4, 14, 23, 25, 28, 805; 424/6, 71, 78

[56] References Cited

U.S. PATENT DOCUMENTS

| | | | |
|---|---|---|---|
| 3,860,484 | 1/1975 | O'Malley | 435/188 |
| 3,964,870 | 6/1976 | Tiedemann et al. | 435/14 |
| 4,038,485 | 7/1977 | Johnston et al. | 435/4 |
| 4,160,008 | 7/1979 | Fenocketti et al. | 422/56 |
| 4,258,001 | 3/1981 | Pierce et al. | 422/56 |
| 4,260,777 | 4/1981 | Rittersdorf et al. | 436/86 |
| 4,301,115 | 11/1981 | Rapkin et al. | 435/805 |
| 4,307,188 | 12/1981 | White | 436/528 |
| 4,336,330 | 6/1982 | Bauer | 435/805 |
| 4,339,242 | 7/1982 | Magers et al. | 436/94 |
| 4,390,621 | 6/1983 | Bauer | 435/805 |
| 4,532,107 | 7/1985 | Siddigi | 422/56 |
| 4,551,306 | 11/1985 | Douwman et al. | 422/56 |
| 4,622,207 | 11/1986 | Wang | 422/56 |
| 4,738,823 | 4/1988 | Englemann | 422/56 |

FOREIGN PATENT DOCUMENTS 0209995 12/1983 Japan .................. 435/4

Primary Examiner—Esther L. Kepplinger
Assistant Examiner—Carol A. Spiegel
Attorney, Agent, or Firm—Parkhurst, Wendel & Rossi

[57] ABSTRACT

A test device having the following meritorious effects is obtained in accordance with the present invention by using at least one composition selected from the group consisting of ink compositions for detecting glucose, for detecting protein, for detecting urobilinogen, and for detecting occult blood in a body fluid, and for detecting the pH thereof:

a) The test device is stable during storage in atmospheric air for a long period of time, presenting no discoloration phenomenon;

b) The test device has high sensitivity coupled with excellent measurement performance;

c) The regions for detecting glucose and the other body fluid ingredients and the pH can be formed directly on the surface of the test device by printing, allowing the test device to be formed by mass production and the process steps to be reduced; and d) The ink compositions for detecting glucose, etc. are stable, and can be handled easily.

5 Claims, 2 Drawing Sheets

TEST DEVICE FOR DETECTING GLUCOSE, PROTEIN UROBILINOGEN, AND/OR OCCULT BLOOD IN BODY FLUIDS AND/OR DETERMINING THE PH THEREOF

This is a continuation of application Ser. No. 06/703,480 filed Feb. 20, 1985, now abandoned.

TECHNICAL FIELD OF THE INVENTION

The present invention relates generally to test devices capable of easily detecting a variety of ingredients in body fluids, and more particularly to a test device capable of detecting glucose, protein, occult blood and urobilinogen in a body fluid and the pH thereof simply, quickly, and moreover simultaneously.

BACKGROUND OF THE INVENTION

In the detection, diagnosis and treatment of diseases, it is highly important to simply and quickly detect the presence of certain ingredients contained in blood, lymph, urine and other body fluids while determining the quantity thereof.

For example, quick and simple determination of the quantity of glucose in a body fluid such as urine or blood is a prime desideratum to the early detection, diagnosis and control of diabetes. Quick and simple determination of the quantity of the protein in a body fluid, particularly urine assumes an important role in the early detection, diagnosis and treatment of gastropathy. Accurate determination of the pH of a body fluid, particularly urine, can aid not only in detection of the presence of protein therein but also in confirmation of the possible bacteriuria which induces pyelitis, cystitis and like urosis. Further, detection of the presence of occult blood in a body fluid, particularly urine, contributes greatly to the early detection, diagnosis and treatment of nephropathy, while determination of the quantity of urobilinogen in a body fluid, particularly urine, holds an important position in the diagnosis of hepatic insufficiency.

As indicated above, it is of crucial importance to simply and quickly detect glucose, protein, occult blood and urobilinogen in a body fluid, particularly urine, or determine the pH of the body fluid. For this purpose, an indicator strip comprising an indicator reagent-impregnated filter paper affixed to a support has heretofore been used in most cases. This type of indicator strip has the advantageous features that it can be handled easily and that the results can be obtained in a short period of time.

In an indicator strip for detecting glucose in a body fluid, especially urine, the glucose entrapped therein reacts with oxygen in the air through action of a glucose-oxidizing enzyme to be finally oxidized into gluconic acid and hydrogen peroxide. The hydrogen peroxide, in turn, generates nascent oxygen through the action of peroxidase, which oxygen reacts immediately with an oxidizable indicator such as o-tolidine to cause the indicator to form color.

The indicator strip for detecting glucose in a body fluid based on the above mechanism was prepared by dissolving or dispersing in water or a water-alcohol solvent system a reagent composition comprising a glucose oxidase, peroxidase and an oxidizable indicator, impregnating a filter paper with the resultant solution, drying the filter paper, causing the filter paper to adhere to a plastic film, and cutting the laminate thus formed to a suitable size.

This method, however, is accompanied by the following problems.

(a) In the case where an impregnant solution is prepared by dissolving or dispersing in water or a water-alcohol solvent system a reagent composition comprising a glucose oxidase, peroxidase and an oxidizable indicator, the enzyme is unstable and hence is liable to be deactivated while the impregnant solution deteriorates rapidly. For this reason, multiple-step impregnation of the filter paper is required immediately after the preparation of the impregnant solution. There remains another problem that, even if the impregnation of the filter paper is promptly carried out, a part of the enzyme is deactivated and a part of the impregnant solution deteriorates.

(b) Since the impregnant solution is unstable, and also complicated process steps are required as has been set forth hereinabove, it is difficult to maintain uniform quality of the product indicator strip, particular caution and skill are required in order to secure the precision and reliability of the indicator strip, the process efficiency tends to be lowered, and the production costs are raised.

Accordingly, there have been attempts to develop indicator strips which can be obtained by a simplified process and is suitable for mass production. Japanese Patent Pub. No.25953/1969 discloses a process for the fabrication of indicator strips by dissolving enzymes in a water-alcohol solvent mixture in advance, admixing therewith an indicator, a pH buffer, a polymer binder and a water-absorptive carrier to prepare an ink composition suitable for printing or coating, applying the ink composition onto a support by printing (including coating), and drying the ink composition thus applied onto the support. In this process, however, enzymes partly dissolved in water are unstable and become rapidly deactivated, so that printing must be carried out immediately after the preparation of the ink composition while at the same time the ink composition must be dried at a low temperature to prevent deactivation of the enzymes and the residual water content of the applied reagent layer must be minimized to obtain good shelf life.

Under the circumstances, we have proposed in Japanese Patent Laid-Open Pub. No.209995/1983 a process for the fabrication of indicator strips by dispersing enzymes in a nonaqueous solvent which does not substantially dissolve the enzymes, and subsequently dissolving or dispersing an indicator, a buffer, a binder and a water-absorptive carrier to prepare an ink composition, and applying the ink composition onto a support by printing. In accordance with this process, an indicator strip exhibiting remarkable ability to measure the quantity of glucose and also having high sensitivity can be obtained, but this indicator strip, when exposed to the air for a long period of time, turns color gradually. Since the color turning reaction of the indicator strip during storage in the air may lead to an incorrect indication in the examination of body fluids, there has been an urgent demand for a solution to this problem.

As a result of our research conducted in an effort to solve the problem set forth hereinbefore, we have found that the color turning reaction of the aforementioned indicator strip for detecting glucose is attributable to the effect of peroxides and the like present in the air in trace amounts on the reagent composition, particularly the oxidizable indicator contained therein. As a result of our subsequent research, we have further found that this color reaction can be inhibited by adding a stabilizer to the reagent composition, and that stabilizer compounds having adequate antioxidant activity and specific surfactants are especially remarkable stabilizers.

On the other hand, an indicator strip for detecting protein in a body fluid, particularly urine, has been conventionally fabricated by immersing a water-absorptive carrier in a solution comprising an indicator which indicates a protein error and a buffer, drying the carrier, and adhering the carrier to a support. This process, however, is still accompanied by the problem that the process steps are complicated. Thus, an indicator strip for detecting protein which can be obtained by a simplified process has been proposed. For example, Japanese Utility Model Laid-Open Pub. No.79767/1982 discloses an indicator strip for detecting protein fabricated by applying on a support a reagent composition comprising a pH indicator, a buffer, a binder and a water-absorptive powder by means of pattern printing. However, this indicator strip has the drawbacks that, due to low permeability and poor water retention, protein in a body fluid does not contact with the portion of the indicator strip where the reagent has been applied and hence the sensitivity of the strip is low and it takes a long time to form color after the strip is immersed in a body fluid. Another drawback of this indicator strip is that a fading phenomenon is conspicuously observable when the reagent portion of the strip which has been immersed in a body fluid to be tested is dried.

As a result of our intensive investigation pursued to solve the above described problems, we have found that, by adding an ion exchange resin having an affinity for protein and also exhibiting adsorptive action to a reagent composition for detecting protein, all of the problems incident to the conventional indicator strips can be solved, thus providing a highly sensitive indicator strip for detecting protein capable of forming a distinct color in a short period of time, which color undergoes almost no fading after drying.

An indicator strip for determining the pH of a body fluid, particularly urine, has hitherto been produced by impregnating a water-absorptive support with an aqueous solution containing a plurality of pH indicators and thereafter drying. This indicator strip has the disadvantage of high production costs due to complicated process steps and hence difficult process control. In order to eliminate this disadvantage, an indicator strip for the pH determination which can be obtained by a simplified process has been proposed. Japanese Patent Pub. No. 25953/1969, for instance, describes an indicator strip comprising a plurality of pH indicators and an adsorptive powder both adhered to a support. This indicator strip is again accompanied by the problems set forth hereinbelow.

(a) When the indicator strip is immersed in a body fluid to be tested and then dried, a color which has once been formed fades conspicuously.

(b) When the indicator strip is immersed in a body fluid to be tested, the indicators may sometimes be eluted into the body fluid, so that a distinct color may not be formed in some cases.

(c) When the indicator strip is immersed in a body fluid to be tested, it takes a long time to form color.

We have further conducted a research to solve the above problems and found that all of these problems can be solved by applying an ink composition for the pH determination comprising a pH indicator, a quaternary ammonium salt or an amine salt, a binder, a water-absorptive powder and a solvent onto a support.

As mentioned previously, it is important to determine the quantity of occult blood or urobilinogen in a body fluid, particularly urine, in checking the renal or hepatic function. An indicator strip for detecting occult blood or urobilinogen has been conventionally formed by coating a support with a reagent composition for use in the detection comprising an indicator for detecting either one of the body fluid ingredients, a water-absorptive carrier and water or a water-alcohol solvent mixture. In the case where water or a water-alcohol solvent mixture is incorporated in a reagent composition, however, the composition thus applied onto the support must be heated to a considerably high temperature in the subsequent drying step. For this purpose, a drying apparatus is required, and, on the other hand, there is a possibility of the indicator for detecting occult blood or urobilinogen deteriorating or becoming denatured.

As a result of our extensive research, we have found that the foregoing problem can be completely solved by using, in the case of occult blood detection, a reagent composition comprising an oxidizable indicator, an organic peroxide, an occult blood detection composition binder and a nonaqueous solvent for the occult blood detection composition; and in the case of urobilinogen detection, a reagent composition comprising a color precursor which forms color by reaction with urobilinogen, a strongly acidic buffer, a urobilinogen detection composition binder and a nonaqueous solvent for the urobilinogen detection composition.

The present invention is also directed to a test device for body fluids comprising a support having printed or coated thereon at least one detection region, each detection region comprising an ink composition selection from the group of ink compositions consisting of:

(a) a glucose detection reagent in accordance with the present invention;

(b) a protein detection reagent in accordance with the present invention;

(c) a pH determination reagent in accordance with the present invention;

(d) an occult blood detection reagent in accordance with the present invention; and (e) an urobilinogen detection reagent in accordance with the present invention.

Finally, the present invention is also directed to a test device comprising a support having printed or coated thereon at least one detection region, wherein water-retentive pattern portions are formed around each of said detection regions.

SUMMARY OF THE INVENTION

The present invention has been developed on the basis of the various discoveries set forth hereinabove, and the objects thereof are as follows:

(A) To provide a test device which is provided with at least one region capable of detecting glucose, protein, occult blood, and urobilinogen in a body fluid, particularly urine, and the pH thereof, and which is capable of detecting these ingredients and the pH simply, quickly, and moreover simultaneously.

(B) To provide a test device having a glucose detection region which has high sensitivity coupled with excellent measurement performance and presents no fading or discoloration phenomenon upon exposure to the air for a long period of time, and which is formable by application methods, particularly printing methods.

(C) To provide a test device having a protein detection region which has high sensitivity, and can form a distinct color in a short period of time, and which is formable by application methods, particularly printing methods, the distinct color, once being formed, undergoing almost no fading or discoloration after drying.

(D) To provide a test device having a pH determination region which can form a distinct color in a relatively short period of time and is formable by application methods, particularly printing methods, the distinct color, once being formed, undergoing almost no fading or discoloration after drying.

(E) To provide a test device having an occult blood or urobilinogen detection region which requires no drying at a high temperature, where no denaturation or deterioration of the indicator incorporated therein occurs, and which is formable by application methods, particularly printing methods.

A distinguishing feature of the test device for body fluids according to the present invention is that it is provided on a surface thereof with a region printed or coated with at least one of the ink compositions (a) through (e) each comprising the following ingredients.

(a) An ink composition for detecting glucose which comprises a reagent composition comprising a glucose oxidase, peroxidase, an oxidizable indicator, a glucose detection composition binder and a stabilizer, dissolved or dispersed in a nonaqueous solvent for the glucose detection composition.

(b) An ink composition for detecting protein which comprises a reagent composition comprising a pH indicator, a pH buffer, a protein-adsorptive ion exchanger, and a protein detection composition binder, dissolved or dispersed in a solvent for the protein detection composition.

(c) An ink composition for pH determination which comprises a reagent composition comprising a pH indicator, a quaternary ammonium salt or an amine salt and a pH determination composition binder, dissolved or dispersed in a solvent for the pH determination composition.

(d) An ink composition for detecting urobilinogen which comprises a reagent composition comprising a color precursor which forms color by reaction with urobilinogen, a strongly acidic buffer, a urobilinogen detection composition binder and a non-aqueous solvent for the urobilinogen detection composition; and (e) An ink composition for detecting occult blood which comprises a reagent composition comprising an oxidizable indicator, an organic peroxide, an occult blood detection composition binder and a non-aqueous solvent for the occult blood detection composition.

A preferred embodiment of the test device for body fluids according to this invention is provided on a surface thereof with a glucose detection region printed or coated with the above described ink composition for detecting glucose, a protein detection region printed or coated with the ink composition for detecting protein and a pH determination region printed or coated with the ink composition for the pH determination, as well as an optional urobilinogen detection region printed or coated with the ink composition for detecting urobilinogen or an optional occult blood detection region printed or coated with the ink composition for detecting occult blood.

The present invention is also directed to a test device for body fluids comprising a support having printed or coated thereon at least one detection region, wherein water-retentive pattern portions are formed around each of said detection regions.

DETAILED DESCRIPTION OF THE INVENTION

The a test device for body fluids in accordance with the present invention is provided on a surface thereof with a region printed or coated with at least one ink composition selected from the group consisting of an ink composition for detecting glucose, an ink composition for detecting protein and an ink composition for detecting pH, and an optional region printed or coated with an ink composition for detecting urobilinogen or for detecting occult blood.

The respective ink compositions will now be described in detail.

(1) Ink Composition for Glucose Detection a) Mechanism

Glucose in a body fluid reacts with oxygen in the air by the action of a glucose-oxidizing enzyme such as glucose oxidase to be finally oxidized into gluconic acid and hydrogen peroxide. The hydrogen peroxide thus produced generates nascent oxygen by the action of peroxidase, which oxygen reacts immediately with an oxidizable indicator such as o-tolidine to cause the indicator to form color. The presence and approximate quantity of glucose in a body fluid are semi-quantitatively determined by the degree of the color formation.

b) Glucose oxidase

Glucose oxidase is used in the state of purified lyophilized products. It is desirable that this enzyme be present in the ink composition in a quantity of from 0.02 to 2% (by weight, as in all percentages and parts set forth hereinafter), preferably from 0.2 to 1.8% of the solid content of the ink composition when an enzyme having an enzymatic activity of 100 units/mg is used.

c) Peroxidase

Peroxidase is an enzyme which catalyzes the oxidation of various organic substances by hydrogen peroxide or organic peroxides. Peroxidase is mainly extracted from horseradish. It is desirable that this enzyme be present in the ink composition in a quantity of from 0.002 to 1%, preferably from 0.02 to 0.2% of the solid content of the ink composition when a lyophilized product having an activity of 100 units/mg is used.

d) Oxidizable indicator

The oxidizable indicator forms color by oxidizing by oxygen, and known compounds such as benzidines and N-alkylated benzidines can be widely used. Among such oxidizable indicators, o-tolidine is particularly preferred. Other one-component-type indicators for use herein are 3,3′,5,5′-tetramethylbenzidine, p-anisidine, N,N-dimethyl-p-phenylenediamine, 2,7-diaminofluorene, 2,2′-azinobis (3-ethyl-benzothiazoline-6-sulfonic acid), 2,6-dichlorophenol, α-naphthol, guaiacum resin, and KI. Among these compounds, guaiacum resin is particularly preferrred.

Binary component indicators comprising a combination of a developer and a coupler can also be used. Examples of the developers are 4-amino-antipyrine, 3-methyl-2-benzothiazolinone hydrazine. N,N-dimethyl-p-phenylenediamine, and tetramethylbenzidine. Examples of couplers are anilines such as dimethylaniline, diethylaniline, N-methyl-N-hydroxyethylaniline, N-methyl-N-hydroxyethyl-m-toluidine and N,N-dimethyl-m-anisidine; phenols such as phenol, p-chlorophenol, 2,6-dichlorophenol, guaiacol, pyrogallol, and o-phenylphenol; and naphthols such as 1,7-dihydroxynaphthalene, 1-naphthol-3,6-disulfonic acid, 1,8-dihydroxynaphthalene-3,6-disulfonic acid, and 8-amino-1-naphthol-3,6-disulfonic acid. Desirably, the oxidizable indicator is present in a quantity of from 0.05 to 10%, preferably from 0.6 to 6% of the solid content of the ink composition.

e) Glucose detection composition binder

The binder should not affect the ingredients or pH of a body fluid to be tested, or the reagents, particularly the enzyme and oxidizable indicator, nor prevent the color formation reaction.

Examples of binders which have been confirmed to meet these requirements are: (i) synthetic resins such as polyester resins, alkyd resins, polyurethane resins, polystyrene resins, acryl resins, epoxy resins, vinyl chloride resin, vinyl chloride copolymer resins, polyvinyl butyral resins, polyvinyl alcohol resins, polyvinyl pyrrolidone resins, and maleic anhydride copolymers; (ii) cellulose derivatives such as methyl cellulose, ethyl cellulose, hydroxyethyl cellulose, and carboxymethyl cellulose; and (iii) natural polymers such as starch, polysaccharides, gelatin, casein, and sodium alginate. The mixtures of these binders may be used.

The binder is advantageously used in a quantity of from 0.1 to 20%, preferably from 0.5 to 10% of the solid content of the ink composition.

f) Stabilizer

A stabilizer contributes to the stabilization of a reagent composition comprising a glucose oxidase, peroxidase, an oxidizable indicator and a binder. Among these, the oxidizable indicator tends to turn color due to the effects of peroxides and the like present in the atmospheric air, as described above. The main role of the stabilizer is to prevent the discoloration. Such stabilizers for use herein are compounds having an appropriate antioxidant activity, specific surfactants represented by glycerol esters and mixtures thereof.

Examples of substances exhibiting an antioxidant action are: radical scavengers such as 2,6-di-t-butylmethoxyphenol, p-methoxyphenol, 1-naphthol, pentamethyl phenol, 2,2,5,7,8-pentamethyl6-hydroxycoumarone and tocopherols; and reducing agents such as ascorbic acid. These substances may inhibit the present reaction for the glucose, detection (oxidation reaction of the oxidizable indicator) and reduce the sensitivity. Accordingly, it is preferable to use such antioxidizing substances that they do not inhibit such a reaction and they can reduce the actions by virtue of peroxides or the like present in the atmospheric air. Preferred antioxidizing substances are radical scavengers. Among these, tocopherols (α-, β-, γ- and δ-) are particularly effective. The quantity of the tocopherols to be added to the ink composition is preferably 0.02 to 0.2% of the solid content of the ink composition. If the stabilizer of this type is added in a quantity of less than 0.02%, the color formation phenomenon in the atmospheric air cannot be effectively prevented. If the quantity is in excess of 0.2%, the color reaction starts to be adversely affected and the sensitivity of the indicator material will be lowered.

Besides the above substances exhibiting an antioxidant action, other additives preventing the color formation phenomenon of the reagent reaction layer in the atmospheric air are specific surfactants represented by glycerol esters although the mechanism is not apparent. Examples of such glycerol esters are glycerol fatty acid esters such as glycerol monoacetate, glycerol diacetate, glycerol monostearate, glycerol monopalmitate, glycerol monooleate, and glycerol monolaurate. It is preferable that the glycerol ester be present in a quantity of from 0.5 to 3% of the solid content of the ink composition. If the quantity of the glycerol ester is less than 0.5%, the color formation phenomenon in the atmospheric air cannot be effectively prevented. Since the glycerol esters scarcely affect the color reaction of the oxidizable indicator adversely, these esters can be employed in an excess quantity.

g) Nonaqueous solvent for the glucose detection composition

The above ingredients are dissolved or dispersed in a nonaqueous solvent which contains substantially no water. Examples of the nonaqueous solvents are (a) aromatic hydrocarbons such as benzene and toluene; (b) aliphatic hydrocarbons such as methyl ethyl ketone; (c) esters such as ethyl acetate; and (d) alcohols such as n-butanol. Among the alcohols, lower alcohols ($C_1$ to $C_2$) are undesirable because they deactivate enzymes.

Heretofore, enzymes have been considered to be unstable and liable to be denatured in an organic solvent, and thus it has been quite unexpected that the ink composition for glucose detection comprising a freeze-dried enzyme dispersed in the nonaqueous solvent mentioned above is stable and not readily denatured. While the reason for this is not clear, it may be presumed that water-soluble enzymes are not dissolved in a nonaqueous solvent but, are only dispersed therein, so that the active site of the protein constituting the enzyme in a dispersed state and the structure thereof are hardly displaced and, if displaced in the vicinity of the interface between the enzyme and the solvent, the solvent cannot easily permeate into the interior of the enzyme, whereby the majority of the enzyme is not deactivated.

Thus, it is preferable that the nonaqueous solvent contain substantially no water and, for this reason, be dehydrated prior to use.

h) Other ingredients

In addition to the above listed ingredients, a water-absorptive powder or a wetting agent may be incorporated in the ink composition for glucose detection, if desired.

The incorporation of the water-absorptive powder increases the water-absorptivity of the ink composition applied onto the support, promotes the contact between the body fluid to be tested and the reagent composition, and further promotes the color reaction of the indicator.

A powder which shows extreme acidity or alkalinity when it comes into contact with water is unsuitable for use as the water-absorptive powder, while a powder having a high degree of whiteness is preferred. Specific examples of the water-absorptive powder are: kaolin, synthetic silica, glass, cellulose block, microcrystalline cellulose, ion exchange cellulose, ion exchange resin, calcium carbonate, magnesium carbonate, and aluminum silicate. It is preferable that the water-absorptive powder be present in a quantity of from 30 to 90% of the solid content of the ink composition.

Examples of the wetting agents are nonionic surfactants, anionic surfactants, cationic surfactants, ampho­teric surfactants, and polyethylene glycols. The wetting agent serves to disperse the reagents, thus promoting the formation of a homogeneous reagent layer, and can improve the wettability of the indicator material. Pref­erably, the wetting agent is present in a quantity of from 0.5 to 5% of the solid content of the ink composition.

Further, a background colorant such as Oil Yellow may also be added to make the tone of the color formed by the indicator more easily distinguishable.

When a glucose detection region is formed by the ink composition for detecting glucose comprising the ingre­dients as described above to detect glucose in a body fluid, reducing materials such as ascorbic acid, glutathi­one and cystein do not adversely affect the color reac­tion even if such reducing materials are present in a body fluid to be tested.

(2) Ink Composition for Protein Detection a) Mechanism

When an indicator which is maintained in the acidic pH range and indicates a protein error (e.g., Tetra­bromophenol Blue) is caused to contact with protein in a body fluid to be tested, the indicator and protein form a complex, turning from the acidic color yellow to the basic color blue. The degree of this color change de­pends upon the quantity of protein in the body fluid to be tested. The presence of protein in the body fluid to be tested is detected on the basis of this mechanism.

b) pH Indicator

This indicator behaves in accordance with the above described mechanism. Specific examples of the indica­tor are: Tetrabromophenol Blue, Tetrabromothymol Blue, ethyl esters of tetrabromophenolphthalein, tetra­bromobenzalaniline, and Bromothymol Blue. Among these indicators, Tetrabromophenol Blue is particularly preferred from the point of view of sensitivity.

c) pH Buffer

The pH buffer is used to maintain the pH of the ink composition in the vicinity of the pH value where the indicator which indicates a protein error changes color. The pH buffer is any buffer that can give the reagent composition a predetermined pH value (e.g. pH 3 to 4). Specifically, a combination of citric acid and sodium citrate is preferably used.

If an excessive quantity of the acidic pH buffer or the indicator is present, however, the color reaction which indicates a protein error may sometimes be inhibited, so that the quantity thereof should be as small as possible.

When Tetrabromophenol Blue is used as the indicator, it is preferable that the pH buffer be present in a quan­tity of from 0.02 to 0.1% of the solid content of the ink composition.

d) Protein-adsorptive ion exchanger

Such ion exchangers are strongly acidic cation ex­changers (functional group: $-SO_3M$), weakly acidic cation exchangers ($-COOM$), strongly basic anion exchangers ($-NR,-X^-$, $-N^+(CH_3)_2(CH_2CH_2O)$), weakly basic anion exchangers ($-N(R)_2$, $-NH(R)$, $-NH_2$ and the like) and the like. Particularly preferred are hydrophilic ion exchangers which are weakly acidic cation exchangers, having $-COOM$ (wherein M is hydrogen or Na) as a functional group and, when the ion exchangers of this type are used, the sensitivity and the color density can be improved.

The base materials of the ion exchangers mentioned above are synthetic resins such as styrene resins and acrylic resins, cellulose and silica.

In this case, the ion exchanger is contained in a rea­gent reaction layer which is immersed in a body fluid to be tested, the base materials are preferably hydrophilic and have excellent water-retentivity. It is preferable that the ion exchanger having styrene-type base materi­als has a low degree of crosslinking (divinyl benzene content of no more than 8%) from such a standpoint.

The cellulose-based material is particularly preferred because water retentivity is largest.

Such cellulose base materials include fibrous materi­als and microgranular materials. When the microgranu­lar materials are used as the base materials, most excel­lent results are obtained in the sensitivity and color density. This is because such microgranular materials have a largest adsorption capacity for protein.

The ion exchanger used herein preferably has an ion exchange capacity of from 0.1 to 5 meq/g (dry resin). The quantity of the ion exchanger, though variable with the ion exchange capacity of the particular ion ex­changer used, is preferably present in a quantity of from 5 to 30% of the solid content of the ink composition in the case where carboxymethyl cellulose exchanger hav­ing an ion exchange capacity of 1.0 meq/g (preferably microgranules) is used.

By adding the ion exchanger to the reagent composi­tion, it is possible to detect 5 to 10 mg/dl of protein in urine, if used as a body fluid to be tested.

e) Protein detection composition binder

The binder should not affect the ingredients or pH of a body fluid to be tested, or the reagents, particularly the indicator, nor prevent the color formation reaction of the indicator.

Examples of binders which have been confirmed to meet these requirements are: (i) synthetic resins such as polyester resins, alkyd resins, polyurethane resins, poly­styrene resins, acryl resins, vinyl chloride resins, vinyl chloride copolymer resins, polyvinyl butyral resins, polyvinyl alcohol resins, and maleic anhydride copoly­mer resins; (ii) cellulose derivatives such as methyl cel­lulose, ethyl cellulose, hydroxyethyl cellulose, and car­boxymethyl cellulose; and (iii) natural polymers such as starch, polysaccharides, gelatin, casein, and sodium alginate.

Among these binders, maleic anhydride copolymer resins such as methyl vinyl ether/maleic anhydride copolymers, isobutylene/maleic anhydride copolymers or styrene/maleic anhydride copolymers, esterified with alcohols are preferred.

It is preferable that the binder be present in a quantity of from 0.5 to 10% of the solid content of the ink composition.

f) Solvents for the protein detection composition

The solvents are preferably those capable of uniformly and stably dissolving or dispersing the above stated reagents, particularly binders.

Solvents which meet this requirement are nonaqueous solvents such as aromatic hydrocarbons, aliphatic hydrocarbons, esters and alcohols; water, or mixture thereof.

It is preferable to use a nonaqueous solvent since a drying step can be carried out at a low temperature for a short period of time after the ink composition for protein detection has been applied onto the support. When a nonaqueous solvent is used, it is also possible to prevent the denaturation or deterioration of the ink composition which is attributed to the residual moisture.

g) Other ingredients

In addition to the above listed ingredients, a water-absorptive powder may be incorporated, if desired. The water-absorptive powder, when incorporated in the reagent reaction.

The binder suitable for the ink composition for the pH determination which meets these requirements is preferably formed by the combination of a water-soluble polymeric material having developing effects, that is, it does not impede the color formation of the pH indicator and moreover stabilizes the color obtained by the color formation and a film-forming water-insoluble polymeric material which does not impede the color formation of the pH indicator and moreover prevents the elution of the reagents into a body fluid to be tested.

The water-soluble polymeric materials described above are (i) natural hydrophilic polymeric materials such as sugar cane starch, potato starch, konjak powder, funori, agar, sodium alginate, gum arabic, dextrin, levan, glue, gelatin, casein and collagen; (ii) semi-synthetic hydrophilic polymeric materials such as cellulose derivatives such as methyl cellulose, hydroxypropyl cellulose, hydroxyethyl cellulose and carboxymethyl cellulose, and starch derivatives such as carboxymethyl starch and dialdehyde starch; and (iii) synthetic polymeric materials such as polyvinyl alcohol, polyacrylamide, polyvinyl pyrrolidone or copolymers thereof, poly(sodium acrylate) and polyethyleneoxide. Among these composition, promotes the contact between the body fluid to be tested and the pH indicator, and also promotes the color reaction of the indicator.

A powder which shows extreme acidity or alkalinity when it comes into contact with water is unsuitable for use as the water-absorptive powder, while a powder having a high degree of whiteness is preferred. Specific examples of the water-absorptive powder are: kaolin, synthetic silica, glass, cellulose block, micro-crystalline cellulose, ion exchange cellulose, ion exchange resin, calcium carbonate, magnesium carbonate, and aluminum silicate It is preferable that the water-absorptive powder be present in a quantity of from 20 to 60% of the solid content of the ink composition.

Further, a small quantity of a wetting agent, such as nonionic surfactants, anionic surfactants, cationic surfactants, amphoteric surfactants and polyethylene glycols, may be also incorporated in the ink composition for protein detection, if desired.

The wetting agent serves to disperse the reagents, thus promoting the formation of a homogeneous reagent layer, and can improve the wettability of the indicator material.

Preferably, the wetting agent is added in a quantity ranging from 0.2 to 10% of the solid content of the ink composition.

The ink composition for protein detection comprising the above ingredients can be prepared as follows.

The buffer, ion exchanger and water-absorptive powder are pulverized into particles 50 $\mu$m or less in size. The powder thus obtained is added to a solvent solution comprising the binder and indicator dissolved or dispersed therein, and then is dispersed and kneaded in a high-speed stirrer, sand mill, ball mill, homogenizer, three rolls, ultrasonic disperser.

(3) Ink Composition for pH Determination a) Mechanism

Preferably a plurality of indicators the tones of which vary with the pH value are used in combination to determine the pH of the body fluid to be tested by judging the tones of the indicators.

b) pH Indicator

Any indicator can be used provided that it is an indicator the tone of which varies depending upon the hydrogen ion concentration of the body fluid to be tested. A plurality of indicators can also be suitably selected or used in combination to determine the pH of wide regions. For example, by using a combination of Methyl Red with Bromothymol Blue as a pH indicator, it is possible to carry out a good pH judgement within the range of pH of from 5 to 9.

It is preferable that the pH indicator be present in a quantity of from 0.01 to 0.8% of the solid content of the ink composition.

c) Quaternary ammonium salt or amine salt

The incorporation of an appropriate quantity of a quaternary ammonium salt in an ink composition inhibits greatly the fading phenomenon of a color which has once been formed and provides a distinct color.

Examples of the quaternary ammonium salts are alkyltrimethyl ammonium salts, alkyldimethylbenzyl ammonium salts, and the like. Among these salts, alkyldimethylbenzyl ammonium salts are particularly preferred.

Primary amine salts, secondary amine salts and tertiary amine salts which are known to be cationic surfactants, or polyethylene glycol can be used in place of the quaternary ammonium salts.

It is preferable that these quaternary ammonium salts or amine salts be present in a quantity of from 0.05% to 1% of the solid content of the ink composition.

d) pH determination composition binder

The binder is used in order to secure the reagents described above and a water-absorptive powder on a support. The binder should not affect the ingredients or pH of a body fluid to be tested. Further, the binder should prevent the elution of the reagents and should not impede or obstruct the color formation compounds, the cellulose derivatives such as hydroxyethyl cellulose and the synthetic polymeric materials such as polyvinyl pyrrolidone are particularly preferred.

On the other hand, the film-forming water-insoluble polymeric materials described above are: (i) cellulose resins such as nitrocellulose, cellulose acetate, ethyl cellulose and cellulose acetate butyrate; and (ii) polyester resins, alkyd resins, polyurethane resins, epoxy resins, acrylic resins, vinyl chloride resins, vinyl chloride copolymer resins, polyvinyl butyral resins, polyvinyl acetate emulsions, vinyl acetate copolymer emulsions (such as vinyl acetate-acrylic ester copolymer emulsion), acrylic ester copolymer emulsions, vinylidene chloride copolymer emulsions, epoxy resin emulsions and synthetic rubber latex. Among these compounds, urethane resins and polyvinyl butyral are preferred because they do not affect the color reaction of the pH indicator.

It is preferable that the binder be present in a quantity of from 2 to 18% of the solid content of the ink composition.

(e) Solvents for the pH determination composition

The solvents are preferably those capable of uniformly and stably dissolving or dispersing the reagents described above, particularly binders. Solvents which meet this requirement are nonaqueous solvents such as aromatic hydrocarbons, aliphatic hydrocarbons, esters and alcohols; water, and mixtures thereof.

It is preferable to use a nonaqueous solvent since a drying step can be carried out at a low temperature for a short period of time after the ink composition for the pH determination has been applied onto the support. When a nonaqueous solvent is used, it is also possible to prevent the denaturation or deterioration of the ink composition which is attributed to the residual moisture.

f) Other ingredients

In addition to the above listed ingredients, a water-absorptive powder may be incorporated, if desired. The incorporation of the water-absorptive powder in the ink composition promotes the contact between the body fluid to be tested and the pH indicator and further promotes the color reaction of the indicator.

A powder which shows extreme acidity or alkalinity when it comes into contact with water is undesirable as the water-absorptive powder, while a powder having a high degree of whiteness is preferred. Specific examples of the water-absorptive powders are kaolin, synthetic silica, glass, cellulose block, microcrystalline cellulose, ion exchange cellulose, ion exchange resin, calcium carbonate, magnesium carbonate, and aluminum silicate It is preferable that the water-absorptive powder be present in a quantity of from 30 to 90% of the solid content of the ink composition.

Further, a small amount of wetting agents such as nonionic surfactants, anionic surfactants, cationic surfactants, amphoteric surfactants, and polyethylene glycols can also be optionally incorporated in the ink composition for the pH determination. The wetting agent serves to disperse each reagent, thus promoting the formation of a homogeneous reagent layer, and can improve wettability.

(4) Ink Composition for Urobilinogen Detection a) Mechanism

Urobilinogen, if present in a body fluid, reacts with a color precursor which combines with the urobilinogen to form color, such as p-dimethyl-aminobenzaldehyde, whereby color is formed. the presence of urobilinogen in a body fluid is detected by observing the color formation and determining the degree thereof.

b) Color precursor which forms color by reaction with urobilinogen

Examples of the color precursors which react with urobilinogen to form color are p-dimethylaminobenzaldehyde, p-diethylaminobenzaldehyde, and aromatic diazonium salts such as p-methoxybenzenediazonium tetrafluoroborate and anthraquinonediazonium tetrafluoroborate.

The color precursor is preferably added in a quantity of from 0.5 to 10% of the solid content of the ink composition.

c) Strongly acidic buffer

Since the reaction between urobilinogen and the color precursor mentioned in the preceding paragraph proceeds smoothly in the acidic range, a strongly acidic buffer is incorporated in the ink composition.

Examples of the strongly acidic buffers are metaphosphoric acid, sulfosalicylic acid, hexaminic acid, and oxalic acid.

It is preferable that the strongly acidic buffer be present in a quantity of from 1 to 50% of the solid content of the ink composition.

d) Urobilinogen detection composition binder

The binder should not affect the ingredients or pH of a body fluid to be tested, or the reagents, particularly the color precursor, nor prevent the color formation reaction.

Examples of binders which have been confirmed to meet these requirements are: (i) synthetic resins such as polyester resins, alkyd resins, polyurethane resins, polystyrene resins, acryl resins, epoxy resins, vinyl chloride resin, vinyl chloride copolymer resins, polyvinyl butyral resins, polyvinyl alcohol resins, polyvinyl pyrrolidone resins, and maleic anhydride copolymers; (ii) cellulose derivatives such as methyl cellulose, ethyl cellulose, hydroxyethyl cellulose, and carboxymethyl cellulose; and (iii) natural polymers such as starch, polysaccharides, gelatin, casein, and sodium alginate The binder is advantageously used in a quantity of from 0.5 to 10% of the solid content of the ink composition.

e) Non-aqueous solvents for the urobilinogen detection composition

The solvents are preferably those capable of uniformly and stably dissolving or dispersing the above stated reagents, particularly binders. Solvents which meet this requirement are nonaqueous solvents such as aromatic hydrocarbons, aliphatic hydrocarbons, esters and alcohols; water, and mixtures thereof.

It is preferable to use a nonaqueous solvent since a drying step can be carried out at a low temperature for a short period of time after the ink composition for urobilinogen detection has been applied onto the support. When a nonaqueous solvent is used, it is also possible to prevent the denaturation or deterioration of the reagent composition which is attributed to the residual moisture.

f) Other ingredients

In addition to the above listed ingredients, a water-absorptive powder may be incorporated, if desired. The water-absorptive powder, when incorporated in the ink composition, promotes the contact between the body fluid to be tested and the color precursor, and also promotes the color formation reaction of the color precursor.

A powder which shows extreme acidity or alkalinity when it comes into contact with water is unsuitable for use as the water-absorptive powder, while a powder having a high degree of whiteness is preferred. Specific examples of the water-absorptive powders are: kaolin, synthetic silica, glass, cellulose block, microcrystalline cellulose, ion exchange cellulose, ion exchange resin, calcium carbonate, magnesium carbonate, and aluminum silicate.

It is preferable that the water-absorptive powder be present in a quantity of from 30 to 90% of the solid content of the ink composition.

Further, a small quantity of a wetting agent, such as nonionic surfactants, anionic surfactants, cationic surfactants, amphoteric surfactants and polyethylene glycols, may also be incorporated in the ink composition for urobilinogen detection, if desired.

The wetting agent serves to disperse the reagents, thus promoting the formation of a homogeneous reagent layer, and can improve the wettability of the indicator material.

Preferably, the wetting agent is added in a quantity ranging from 0.5 to 5% of the solid content of the ink composition.

(5) Ink Composition for Occult Blood Detection a) Mechanism

Occult blood, if present in a body fluid, reacts with an organic peroxide such as cumene hydroperoxide to generate nascent oxygen which reacts immediately with an oxidizable indicator such as o-tolidine to cause the indicator to form color. The presence and approximate quantity of occult blood in a body fluid are determined by the degree of the color formation.

b) Oxidizable indicator

The oxidizable indicator forms color by oxidation by oxygen, and known compounds such as benzidines and N-alkylated benzidines can be widely used, with o-tolidine being particularly preferred. Desirably, the oxidizable indicator is present in a quantity of from 0.05 to 10%, preferably from 0.6 to 10% of the solid content of the ink composition.

c) Organic peroxide

Examples of the organic peroxides are cumene hydroperoxide, 2,5-dimethylhexane-2,5-dihydroperoxide, and diisopropylbenzene hydroperoxide, with the cumene hydroperoxide being especially preferred.

The organic peroxide is preferably added in a quantity of from 1 to 50% of the solid content of the ink composition.

d) Occult blood detection composition binder

The binder should not affect the ingredients or pH of a body fluid to be tested, or the reagents, particularly the oxidizable indicator, nor prevent the color formation reaction.

Examples of binders which have been confirmed to meet these requirements are: (i) synthetic resins such as polyester resins, alkyd resins, polyurethane, polystyrene resins, acryl resins, epoxy resins, vinyl chloride resin, vinyl chloride copolymer resins, polyvinyl butyral resins, polyvinyl alcohol resins, polyvinyl pyrrolidone resins, and maleic anhydride copolymers; (ii) cellulose derivatives such as methyl cellulose, ethyl cellulose, hydroxyethyl cellulose, and carboxymethyl cellulose; and (iii) natural polymers such as starch, polysaccharides, gelatin, casein, and sodium alginate.

The binder is advantageously incorporated in the ink composition in a quantity of from 0.1 to 20%, preferably from 0.5 to 10% of the solid content of the ink composition.

e) Non-aqueous solvents for the occult blood detection composition

The solvents are preferably those capable of uniformly and stably dissolving or dispersing the above stated reagents, particularly binders.

Solvents which meet this requirement are nonaqueous solvents such as aromatic hydrocarbons, aliphatic hydrocarbons, esters, and alcohols; water, and mixture thereof.

It is preferable to use a nonaqueous solvent since a drying step can be carried out at a low temperature for a short period of time after the ink composition for occult blood detection has been applied onto the support. When a nonaqueous solvent is used, it is also possible to prevent the denaturation or deterioration of the reagent composition which is attributed to the residual moisture.

f) Other ingredients

In addition to the above listed ingredients, a water-absorptive powder may be incorporated, if desired. The water-absorptive powder, when incorporated in the reagent composition, promotes the contact between the body fluid to be tested and the oxidizable indicator, and also promotes the color reaction of the indicator.

A powder which shows extreme acidity or alkalinity when it comes into contact with water is unsuitable for use as the water-absorptive powder, while a powder having a high degree of white is preferred.

Specific examples of the water-absorptive powders are: kaolin, synthetic silica, glass, cellulose block, microcrystalline cellulose, ion exchange cellulose, ion exchange resin, calcium carbonate, magnesium carbonate, and aluminum silicate.

It is preferable that the water-absorptive powder be present in a quantity of from 30 to 90% of the solid content of the ink composition.

Further, a small quantity of a wetting agent, such as nonionic surfactants, anionic surfactants, cationic surfactants, amphoteric surfactants and polyethylene glycols, may be incorporated in the ink composition for occult blood detection, if desired The wetting agent serves to disperse the reagents, thus promoting the formation of a homogeneous reagent layer, and can improve the wettability of the indicator material. It is preferable that the wetting agent be present in a quantity of from 0.5 to 5% of the solid content of the ink composition.

Further, a background colorant such as Oil Yellow may also be added to make the tone of the color formed by the indicator more easily idstinguishable.

Figure 1:
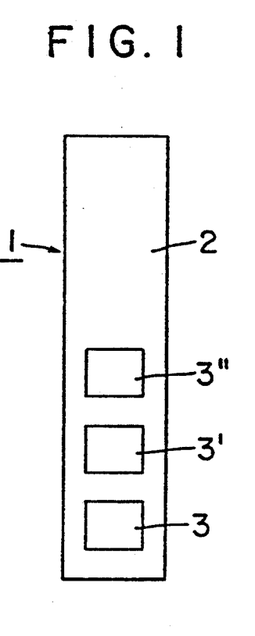
FIG. 1 represents an embodiment of a test device for body fluids according to the present invention wherein a tape-type support is used.

A variety of ink compositions as described above are applied onto a support such as the one shown in FIG. 1, depicted by reference numeral 2 to form a variety of detection regions on the support. Thus, a test device for body fluid according to the present invention is obtained Application techniques suitable for use herein are printing processes, and coating processes (such as roll coating, spray coating, dip coating, solid coating) In the present invention, it is preferable that the quantity of the ink composition applied be relatively large and that the quantity be constant, and therefore the ink composition is preferably applied onto the support by the silk screen printing process, intaglio printing process, gravure printing process and the like. While the quantity of the ink composition applied may vary depending upon the type of the ink composition, in general, the quantity is from 2 to 150 grams per square meter (on a dry basis).

Preferably, the supports neither react with the reagent composition nor prohibit the color formation of the reagent. Specific examples of the supports are papers, synthetic papers, nonwoven fabrics, synthetic resin films, and laminates of paper and synthetic resin film. Specific examples of the materials from which a support is produced are plastic sheets such as polyethylene terephthalate, polystyrene and polyvinyl chloride; nonwoven fabrics of fibers such as polyester, polypropylene and nylon; and papers such as filter paper, art paper and coat paper.

The test device in accordance with the present invention comprises a support with a variety of detection regions which may be in the form of strips, rolls, tapes, sticks and the like. For example, as shown in FIG. 1, a support 2 for a strip-type test device 1 can be provided with detection regions 3, 3' and 3".

If the detection regions 3, 3' and 3" are, for example, a glucose detection region, a protein detection region and a pH detection region, respectively, it is possible to carry out the three tests. The number of the detection regions may vary depending upon the uses of the indicator material. Alternatively, the supports per se may be in the form of containers capable of sampling the body fluid to be tested, such as caps, test tubes, dishes, trays, dropping pipette or bags, and may be provided with detection regions to produce the test device according to the present invention.

Figure 2:
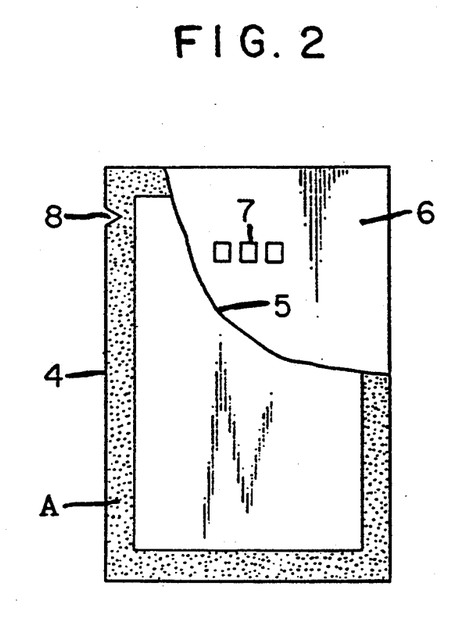
FIG. 2 represents another embodiment of a test device for body fluids according to the present invention wherein a container-type support is used.

FIG. 2 represents an embodiment of a test device which is provided on a container-type support with detection regions according to the present invention. A container 4 is a packaging bag-type support made of gas barrier sheets. The interior is sealed by sealing the portions shown by A in FIG. 2. In order to show the interior, a portion of the packaging bag-type support is removed as illustrated by line 5. The inner surface of a rear sheet 6 is provided with detection regions 7. Thus, in one embodiment of the present invention, the inner surface of the sealed packaging bag made of gas barrier sheets is provided with detection regions. In such an embodiment, in order to make it possible to readily open by tearing, as shown in FIG. 2, a V-shaped notch 8 can be formed. Alternatively, nicks notched about half of the thickness of the sheet can be formed. In these cases, the packaging bag can be opened without using any instrument. In any event, the packaging bag is opened and urine which is a detection object is subjected to sampling. The urine is brought into contact with the detection regions 7 to form color and the resulting color is compared with a previously provided standard color to carry out color judgement.

Figure 3:
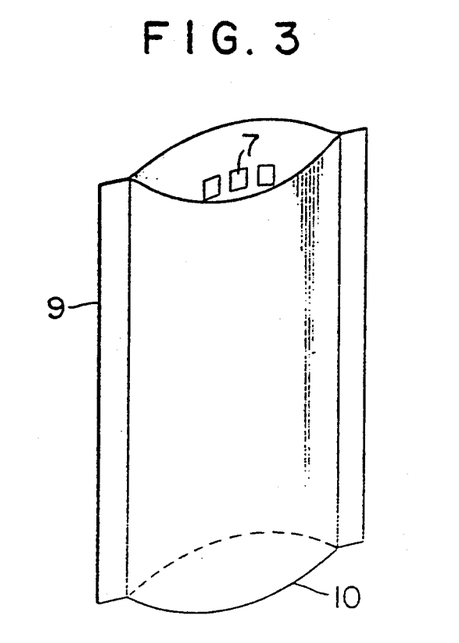
FIG. 3 represents a further embodiment of a test device for body fluids according to the present invention wherein a self-supporting container-type support is used.

A packaging bag-type support 9 having a structure as shown in FIG. 3 can be self-supported because the lower end 10 is in the approximate form of a circle when liquid is poured into the interior of the support, when it is breathed upon or when it is spread with hands. Accordingly, the packaging bag-type support shown in FIG. 3 is suitable for standing at a horizontal place after sampling as opposed to the support shown in FIG. 2.

When applied to a bag such as those shown in FIG. 2 or 3, a tape-type indicator which is prepared by printing on a support different from the bag material may be adhered to the bag with adhesives.

While the support shown in FIG. 2 or 3 may be used as it is, it is possible to previously form standard colors corresponding to various concentrations at the appropriate places of outer surface of the container-type support. Urine is subjected to sampling to cause the urine detection regions to form color. The contents thereof are discarded and thereafter the support is folded again. The resulting color is compared with the standard colors described above. Since the standard colors are formed at the predetermined places, the colored regions are readily compared with the standard colors. The number of the standard colors may vary depending upon detection target substances and their concentrations.

It is necessary that the container-type support for use herein have gas barrier properties. Flexible materials are preferred. The materials from which the support is produced are films of materials such as plain cellophane, polyethylene terephthalate, nylon, polypropylene, polyethylene, and polyvinylidene chloride; composite sheets of these films and other films or papers; and composite sheets incorporating aluminum foil. Specific examples of suitable composite sheets are laminated composite sheets such as plain cellophane/polyethylene, polyvinylidene coat/plain cellophane/polyethylene, polyethylene terephthalate/polyethylene, polycarbonate/polyethylene, oriented polypropylene/polyethylene/plain cellophane/polyethylene, polyvinylidene chloride/polyethylene terephthalate/polyethylene, non-plasticized polyvinyl chloride/polyethylene, oriented polypropylene/polyvinyl alcohol/polyethylene, polypropylene/polyethylene/polyvinylidene chloride, nylon/polyethylene, plain cellophane/polyethylene/aluminum/polyethylene, nylon/polyethylene/aluminum/polyethylene.

When the detection region of the container-type test device described herein is sealed in the container, it is unnecessary to separately provide a detection paper for urine analysis (urinalysis) and the container. The shelf or storage life of the reagent at the detection region is long, and the volume of the container-type test device is small. Accordingly, this will save space during storage.

When, as shown in FIG. 1, a test device provided with a plurality of different target-detection regions is immersed in a body fluid to be tested (such as urine), the analytical reagents of the detection regions are eluted by the body fluid to be tested (usually in a minor amount). Accordingly, the eluted analytical reagents contaminate other detection regions. This contamination impedes or obstructs the color reaction and the error in colored tone may occur.

Thus, the present invention also provides a test device wherein the drawback in using a strip or stick-type test device having a plurality of different target-detection regions (i.e., contamination) can be effectively avoided without any problems in ink application or pattern formation, and wherein it can prevent the droplets of the body fluid from remaining at the surface of the detection regions after the immersed body fluid to be tested is lifted up. For this purpose, it is preferable to form water-retentive pattern portions at the periphery of the plurality of detection regions described above.

Figure 4:
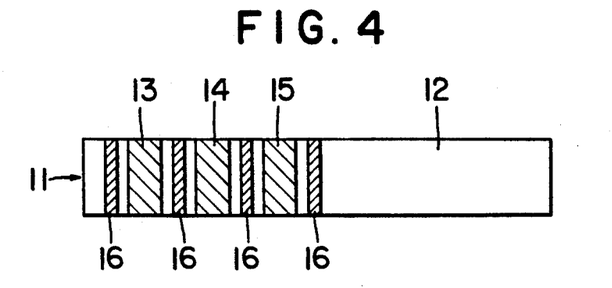
FIG. 4 represents a still further embodiment of a test device for body fluids according to the present invention wherein water-retentive pattern portions are formed at the periphery of detection regions formed on a tape-type support.

FIG. 4 represents a most typical embodiment of such a test device. A strip-type test device 11 has detection regions 13, 14 and 15 on a support 12. The test device has water-retentive pattern portions 16 between the detection regions 13 and 14; between the detection regions 14 and 15; on the left of the detection region 13; and on the right of the detection region 15.

The water-retentive pattern portions 16 (a) prevent the analytical reagent dissolved in the body fluid to be tested from the detection regions from flowing to the adjacent detection regions; and (b) prevent the body fluid to be tested from remaining in the detection regions in the form of droplets.

The water-retentive pattern portions 16 are formed from, for example, materials having excellent hydrophilicity and good "wettability" of the body fluid to be tested, or materials having excellent water absorption.

Examples of the materials having excellent hydrophilicity are water-soluble or water-swelling resins such as carboxymethyl cellulose or its crosslinked products, methyl cellulose, starch ethers, sodium alginate, polyacrylamide, polyethylene oxide, polyvinyl alcohol, and polyvinyl pyrrolidone, or mixtures of at least 2 resins described above, and inorganic fillers such as silica, alumina and calcium carbonate, dispersed in a binder in a quantity of from 5 to 60%, preferably from 10 to 30%.

Examples of the materials having excellent water absorption are (1) foams having open cells and (2) microcrystalline cellulose, dispersed in a binder.

Examples of the binders described above are as follows: cellulose derivatives such as ethylcellulose, ethylhydroxyethylcellulose, cellulose acetate propionate, nitrocellulose, cellulose acetate; styrene resins and styrene copolymer resins such as polystyrene, poly-α-methylene; acrylic or methacrylic homopolymer or copolymer resins such as polymethyl methacrylate, polyethyl methacrylate; rosins, rosin ester resins such rosin-modified maleic acid resin, rosin-modified phenol resin; polyvinyl acetate resin, cumarone resin, vinyl toluene resin, vinyl chloride resin, polyester resin, polyurethane resins, butyrene resin, polyamide resins, vinyl chloride-vinyl acetate copolymer resin, polyvinylidene chloride resin, melamine resins and silicone resins.

When such water-retentive patterns are formed at the periphery of the detection regions, the contamination due to the adjacent detection regions does not occur during testing and the droplets of the body fluid to be tested do not remain on the detection regions. Accordingly, no color shading occurs and therefore color judgement can be accurately carried out.

The support of strip-type indicator material shown in FIG. 4 can be formed from non-absorptive materials such as various plastic sheets, and the water-retentive pattern portions can be formed from highly absorptive materials such as highly water-absorptive polymer having a capacity absorbing pure water of at least 10 times of own weight. The absorptive detection regions 13, 14 and 15 and the highly water-retentive pattern portions 16 are provided at certain intervals, and the non-absorptive material is interposed therebetween. Accordingly, the body fluid such as urine deposited on this strip-type indicator material is adequately subjected to partition between the detection region and the water-retentive pattern portion, and thus the effusion of the analytical reagent from the detection regions can be effectively prevented.

If there is no non-absorptive material between the detection region and the water-retentive pattern portion, the transfer of the reagent occurs between the detection region and the water-retentive pattern portion after immersion in the body fluid, and thus contamination may occur. On the other hand, if only non-absorptive material is present at both the sides of the detection region and if the water-retentive pattern portions are absent, the absorption of the body fluid remaining on the detection regions is inferior. This affects color formation performance. This effect is particularly remarkable at the glucose detection region.

An ink composition from which the water-retentive pattern portions having high water absorption are produced comprises an absorptive powder such as cellulose, starch and highly water-absorptive gel; a hydrophilic or hydrophobic resin; a binder; additives such as inorganic fillers; and a solvent. The highly absorptive gels for use herein are PVA (polyvinyl alcohol), acrylates, acrylonitrile or starch-based crosslinked graft copolymers. Examples of the highly water-absorptive gels commercially available are SUMIKA GEL SP520 having an absorption capacity of 600 times (PVA-acrylate block copolymer manufactured by Sumitomo Kagaku K.K., Japan), SUNWET IM-1000 having an absorption capacity of 1000 times (acrylate graft starch manufactured by Sanyo Kasei K.K., Japan), and KI Gel (reaction product of PVA and cyclic acid anhydride).

In various test devices, each detection region is usually formed by applying one layer of all ingredients of each ink composition onto a support. However, for example, in the case of the ink composition for detecting glucose, it is preferable to form multilayers such as 2 or 3 layers to incorporate ingredients therein. For example, an uppermost layer of saccharide-oxidizing enzyme (A), an intermediate layer of peroxidase (B) and a lowermost layer of oxidizable indicator (C) can be formed on a support by applying them. Further, an upper layer of saccharide-oxidizing enzyme (A) and peroxidase (B), and a lower layer of oxidizable indicator (C) can be formed. Furthermore, an upper layer of the above "A" and "C", and a lower layer of "B" can be formed. Moreover, when the indicator described above comprises "$C_1$" and "$C_2$", an upper layer of "A" and "$C_1$", and a lower layer of "B" and "$C_2$" can be formed. When a plurality of layers containing three components A, B and C described above are formed, the color tone due to the body fluid can be stably retained for a long period of time.

When an indicator material of the present invention is produced by applying various reagents to the support in the form of strips, rolls, tapes, sticks and the like, allowing it to stand in the atmospheric air may lower the function of the analytical reagents through the action of moisture or carbon dioxide in the air. Thus, accurate tests results cannot be obtained. For example, when persons carry out body fluid analysis such as urine analysis at home, the majority of the indicator strips are tested on the basis of the analytical reagents having lowered functions.

In order to prevent such drawbacks, according to the present invention there is provided a packaging container for a strip-type test device wherein the strip-type test device is sealed and packaged by a packaging material having gas barrier properties. By using such a packaging container, the pot life of the strip-type test device becomes long, and appropriate test results can be always obtained.

A packaging container for a strip-type test device according to the present invention will be described hereinafter on the basis of embodiments shown in FIGS. 5 and 6.

Figure 5:
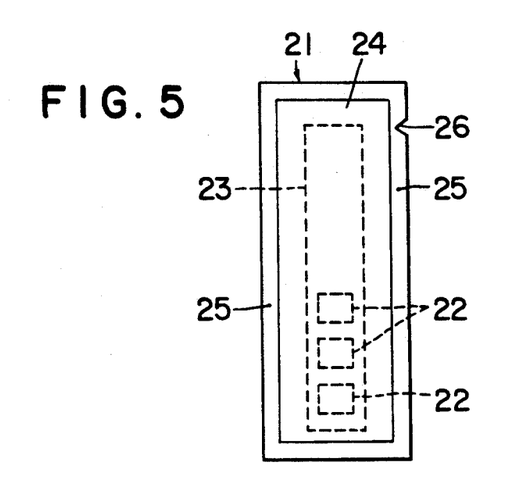
FIG. 5 represents one embodiment of a package for a body fluid test device according to the present invention.

The present packaging container represented by reference numeral 21 in FIG. 5 has such a structure that a single strip-type test device 23 having urine analysis regions 22 is sealed and packaged by a packaging material 24 having gas barrier properties as described above. The portions represented by a reference numeral 25 are heat fusion portions which are circumferential portions of the packaging container 21. A V-shaped broken portion 26 formed in the heat fusion portions described above is a tear end portion for readily opening the packaging container 21.

Figure 6:
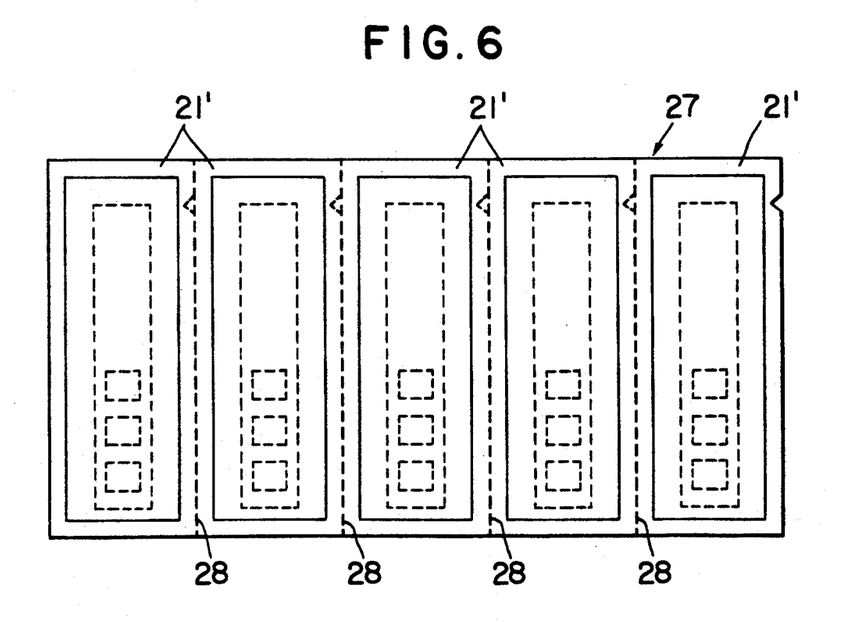
FIG. 6 represents another embodiment of a package for a body fluid test device according to the present invention.

A packaging container 27 for strip-type test devices shown in FIG. 6 is another embodiment of the present invention. This packaging container 27 has such a structure that a plurality of packaging containers 21' having the same structure as that of the packaging container 21 for strip-type test devices shown in FIG. 5 are connected. The adjacent packaging containers 21', 21' are connected by perforation lines 28 formed in the heat fusion portions. Thus, the packaging container 27 has such a structure that it can be readily separated into individual packaging containers 21', 21', 21', 21' and 21'.

When one uses the single packaging container shown in FIGS. 5 and 6 wherein each strip-type test device is sealed and packaged by the packaging material having gas barrier properties, only strip-type indicator material necessary in a urine analysis is first brought into contact with the outside air immediately before use. Accordingly, the present indicator material is not accompanied by a lowered function due to moisture and carbon dioxide in the air. According to the present invention, it is possible to always obtain accurate urine analysis results.

While the present invention will be illustrated by Examples as described hereinafter, the present invention is not limited thereto.

EXAMPLE 1

An ink composition for detecting glucose comprising the following ingredients was prepared by finely dividing and dispersing in a homomixer.

| | Parts by wt. |
|---|---|
| Glucose oxidase (manufactured by Toyo-bo K.K., Japan; Grade II) | 0.50 |
| Peroxidase (manufactured by Toyo-bo K.K., Japan; Grade III) | 0.10 |
| o-Tolidine | 2.0 |
| Butanol ester of isobutylene/maleic anhydride copolymer (manufactured by Kurare Isoprene Chemical, Japan and marketed under the trade name ISOBAN #10) | 2.5 |
| DL-α-tocopherol | 0.1 |
| Polyoxyethylene sorbitan monooleate (manufactured by Kao Sekken K.K., Japan and marketed under the trade name TWEEN 20) | 1.2 |
| Microcrystalline cellulose (manufactured by Asahi Kasei Kogyo K.K., Japan, and marketed under the trade name ABICEL SF) | 30 |
| n-Butanol | 47 |
| Solvent Yellow 6 | 0.05 |
| Citric acid | 3.2 |
| Sodium citrate | 12.0 |

The composition described above was sufficiently finely divided and dispersed in a homomixer, and then applied onto a white polystyrene sheet having a thickness of 250 μm by the screen printing process so that a tetragon having each side of 5 millimeters was formed. A screen plate used was of 100 mesh, and the sum of the thickness of a resist and a screen gauze was 130 μm.

The resulting printed matter was dried for 30 minutes at a temperature of 60° C. and cut into a strip form to produce a test device for detecting glucose.

When the resulting test device was rapidly immersed in urine having a known concentration of glucose, it rapidly formed a distinct color. This indicator material had high sensitivity and exhibited an ability to measure the quantity of glucose within the range of from 20 milligrams per deciliter to 1,000 milligrams per deciliter. The tone after immersion was extremely stable for a long period of time. The tone was determined 30 minutes after immersion, and the results obtained are shown in Table 1.

TABLE 1

| COncentration of glucose present in urine (milligram per deciliter) | Color judgement | |
|---|---|---|
| | Hue | Brightness/ Saturation |
| 0 | 10 YR | 8/10 |
| 20 | 2.5 GY | 6/6 |
| 50 | 10 GY | 5/8 |
| 100 | 10 GY | 4/6 |
| 250 | 10 G | 4/8 |
| 500 | 10 G | 3/6 |

The tone is represented according to the standard tone of JIS Z 87 21. In the above Table, YR refers to a yellow-red intermediate color (i.e., orange) GY refers to a green-yellow intermediate color, and G refers to green.

When a sample to which up to 250 milligrams per deciliter of ascorbic acid was added was used, similar results were obtained. As can be seen from the foregoing, the judgement is not readily affected even if a reducing material is present in the body fluid.

EXAMPLE 2

An ink composition for detecting glucose comprising the following ingredients was prepared in the same manner as that of Example 1.

| | Parts by wt. |
|---|---|
| Glucose oxidase (manufactured by Toyo-bo K.K., Japan; Grade II) | 0.50 |
| Peroxidase (manufactured by Toyo-bo K.K., Japan; Grade III) | 0.10 |
| o-Tolidine | 2.0 |
| Butanol ester of isobutylene/maleic anhydride copolymer (manufactured by Kurare Isoprene Chemical, Japan and marketed under the trade name ISOBAN #10) | 2.5 |
| Glycerol stearate ester (manufactured by Kao Sekken K.K., Japan and marketed under the trade name EXCEL T-95) | 1.5 |
| Polyoxyethylene sorbitan monooleate (manufactured by Kao Sekken K.K., Japan and marketed under the trade name TWEEN 20) | 1.2 |
| Microcrystalline cellulose (manufactured by Asahi Kasei Kogyo K.K., Japan, and marketed under the trade name ABICEL SF) | 30 |
| n-Butanol | 47 |
| Solvent Yellow 6 | 0.05 |
| Citric acid | 3.2 |
| Sodium citrate | 12.0 |

A test device for detecting glucose was produced in the same manner as that of Example 1 using the above ink composition for detecting glucose.

COMPARATIVE EXAMPLE 1

(Effects of Glycerol Esters)

A test device for detecting glucose was produced in the same manner as that of Example 2 except that no glycerol stearate ester was added to the ink composition for detecting glucose. For the concentrations of glucose, color results equal to those of Example 2 were obtained. However, if the test device was allowed to stand for from several hours to several days in the atmospheric air, the test device obtained in Comparative Example 1 exhibited the discoloration of the colored portions The results obtained are shown in Table 2.

TABLE 2

| | Period wherein the test devices were allowed to stand in atmospheric air | | | |
|---|---|---|---|---|
| | 0–1 hr | 3 hours | 2 days | 10 days |
| Exam. No. 2 | yellow | yellow | yellow | slightly yellowish brown |
| Com. Exam. No. 1 | yellow | yellowish green | brown | dark brown |

Even if the test devices obtained in Examples 1 and 2 were stored for a long period of time in a sealed state in a bottle in which a desiccating agent was placed, they were stable and no deterioration in performance was observed.

EXAMPLE 3

An ink composition for detecting glucose comprising ingredients similar to those of Example 1 except that o-tolidine was replaced by guaiacum resin and no Solvent Yellow 6 was used. This ink composition was applied onto a white polystyrene sheet to form a strip-shaped test device for glucose. When this test device was rapidly immersed in urine having the known concentration of glucose, it formed a color. The tone was stable after immersion. The results obtained are shown in Table 3.

TABLE 3

| Concentration of glucose present in urine (milligram per deciliter) | Color judgement | |
|---|---|---|
| | Hue | Brightness/Saturation |
| 0 | 10 Y | 9/2 |
| 20 | 5 GY | 8/2 |
| 50 | 10 G | 7/2 |
| 100 | 7.5 BG | 6/6 |
| 250 | 5 B | 4/6 |
| 500 | 10 B | 3/6 |

In the above Table, BG refers to a blue-green intermediate color and B refers to blue.

EXAMPLE 4

An ink composition for detecting glucose comprising the following ingredients was prepared by finely dividing and dispersing in a homomixer.

| | Parts by wt. |
|---|---|
| Glucose oxidase (manufactured by Toyo-bo K.K., Japan; Grade II) | 0.5 |
| Peroxidase (manufactured by Toyo-bo K.K., Japan; Grade III) | 0.1 |
| 4-Aminoantipyrine | 0.1 |
| Sodium 1-naphthol-3,6-disulfonate | 2.0 |
| Butanol ester of isobutylene/maleic anhydride copolymer | 2.0 |
| DL-α-tocopherol | 2.5 |
| Polyoxyethylene sorbitan monooleate (manufactured by Kao Sekken K.K., Japan and marketed under the trade name TWEEN 20) | 0.1 |
| | 1.2 |
| Microcrystalline cellulose (manufactured by Asahi Kasei Kogyo K.K., Japan and marketed under the trade name ABICEL SF) | 30 |
| n-Butanol | 45 |

-continued

| | Parts by wt. |
|---|---|
| Solvent Yellow 6 | 0.05 |
| Citric acid | 3.2 |
| Sodium citrate | 12.0 |

The ink composition was applied onto a white polystyrene sheet having a thickness of 250 μm by the screen printing process so that a tetragon having each side of 5 millimeters was formed. A screen plate used was of 100 mesh, and the sum of the thickness of a resist and a screen gauze was 130 μm.

The resulting printed matter was dried for 30 minutes at a temperature of 65° C. and cut into a strip form to obtain a test device for detecting glucose.

EXAMPLE 5

An ink composition for detecting protein comprising the following ingredients was prepared by finely dividing and dispersing in a homomixer.

| | Parts by wt. |
|---|---|
| Tetrabromophenol Blue | 0.05 |
| Citric acid | 8.6 |
| Sodium citrate | 3.7 |
| Carboxymethyl ion exchanger (manufactured by Whatman; CM-32) | 13.5 |
| | 13.5 |
| Alcohol ester of isobutylene/maleic anhydride copolymer resin | 2.0 |
| Sorbitan monooleate (manufactured by Kao Sekken K.K., Japan and marketed under the trade name LEODOL SP-L10) | 1.1 |
| Microcrystalline cellulose (manufactured by Asahi Kasei Kogyo K.K., Japan, and marketed under the trade name ABICEL SF) | 25 |
| Butyl cellosolve | 46 |

The composition described above was sufficiently finely divided and dispersed in a homomixer, and applied onto a white polystyrene sheet having a thickness of 250 μm by the screen printing process so that a tetragon having each side of 5 millimeters was formed. The screen plate used was of 100 mesh, and the sum of a resist and a screen gauze was 160 μm. The resulting printed product was dried for 40 minutes at a temperature of 65° C. and cut into a strip form to produce a test device for detecting protein. When the resulting indicator material was rapidly immersed in urine having the known concentration of protein, a slightly yellowish green through blue distinct color was obtained at the substantially same time as that of immersion within the concentration range of from 5 milligrams per deciliter to 2,000 milligrams per deciliter depending upon the concentration of protein. A protein-free solution remained yellow. Further, the tone after immersion was extremely stable for a long period of time.

COMPARATIVE EXAMPLE 2

(Effect of Ion Exchanger)

A test device for detecting protein was produced in the same manner as that of Example 5 except that no carboxymethyl ion exchanger was added and microcrystalline cellulose was increased.

COMPARATIVE EXAMPLE 3

(Effect of Ion Exchanger)

An ink composition for detecting protein comprising the following ingredients was prepared in the same manner as that of Example 5.

|  | Parts by wt. |
|---|---|
| Tetrabromophenol Blue | 0.07 |
| Citric acid | 8.6 |
| Sodium citrate | 3.7 |
| Vinyl acetate resin (Sekisui Kagaku K.K., Japan, and marketed under the trade name ESNEAL C-3) | 5.5 |
| Sorbitan monooleate | 1.2 |
| Microcrystalline cellulose | 38 |
| Solvent mixture of ethyl alcohol with methyl ethyl ketone in a ratio of 3:7 | 43 |

A test device for detecting protein was produced in the same manner as that of Example 5 using such an ink composition.

The protein detection sensitivity and time required for forming color, of the test devices of Example 5 and Comparative Examples 2 and 3 were determined, and the results obtained are shown in Table 4.

TABLE 4

|  | Sensitivity (protein present in urine) | Time required for forming color after immersion |
|---|---|---|
| Example 5 | 5-10 milligrams per deciliter | Immediately |
| Comparative Example 2 | above 30 milligrams per deciliter | Immediately |
| Comparative Example 3 | above 30 milligrams per deciliter | 30 seconds |

EXAMPLE 6

An ink composition for pH determination comprising the following ingredients was prepared.

|  | Parts by wt. |
|---|---|
| Sodium salt of Methyl Red | 0.01 |
| Bromothymol Blue | 0.13 |
| Hydroxyethyl cellulose (manufactured by G.A.F. and marketed under the trade name K-90) | 4 |
| Vinyl butyral resin (manufactured by Dai Nippon Ink K.K., Japan and marketed under the trade name PANDEX T-5670) | 0.5 |
| Alkylbenzyldimethyl ammonium chloride (manufactured by Kao Sekken K.K., Japan and marketed under the trade name Sanizol) | 0.14 |
| Microcrystalline cellulose (manufactured by Asahi Kasei Kogyo K.K., Japan and marketed under the trade name, ABICEL SF) | 36 |
| Ethyl cellosolve | 60 |

The composition described above was sufficiently finely divided and dispersed in a homomixer, and then applied onto a white polystyrene sheet having a thickness of 250 μm by the screen printing process so that a tetragon having each side of 5 millimeters was formed. The screen plate used was of 100 mesh, and the sum of a resist and a screen gauze was 130 μm.

The resulting printed matter was dried for 30 minutes at a temperature of 65° C. and cut into strip form to obtain test devices for pH determination.

These sticks were tested with solutions of known pH. The colors observed at various hydrogen ion concentrations were as follows:

pH 5: orange
pH 6: yellow
pH 7: yellowish green
pH 8: green
pH 9: blue

Colors were uniform and distinct, and easily discriminated within the range of from 5 to 9. Further, no elution of dyestuffs and the like into a body fluid to be tested was observed. Thus, the tone was not changed even if it was allowed to stand for 20 minutes in a room after immersion. Even if it was allowed to stand for several hours to dry the reagent layer, almost the same tone was maintained other than for a pH of 5.

Even in the case of solutions such as urine, the pH can be accurately determined. Even if this indicator material was stored for a long period of time (18 months), color performance did not change and was stable.

Further, the above ink composition for pH determination was stable. Even if a month elapsed after preparation, it was possible to carry out printing by only redispersing, and the resulting test device had good performance as well.

EXAMPLE 7

A test device for pH determination was produced in the same manner as that of Example 6 except that hydroxyethyl cellulose and the polyvinyl butyral resin in the ink composition of Example 6 for pH determination were replaced with polyvinyl pyrrolidone (manufactured by G.A.F. and marketed under the trade name K-90) and a urethane resin (manufactured by Dai Nippon Ink K.K., Japan and marketed under the trade name PANDEX T-5670), respectively. The resulting test device for pH determination exhibited a distinct and stable color within the pH ranges of from 5 to 9 as in Example 6.

COMPARATIVE EXAMPLE 4

(Effect of Quaternary Ammonium Salt)

A test device was produced in the same manner as that of Example 6 except that SANIZOL was not incorporated into the ink composition for pH determination described in Example 6.

After this test device was immersed in a solution to be tested, the change of formed color with the elapse of time was as follows:

| pH | Immediately after immersion | 20 minutes after immersion |
|---|---|---|
| 5 | orange | orange |
| 6 | yellowish orange | orange |
| 7 | yellowish green | yellow |
| 8 | green | yellow |
| 9 | blue | yellow |

Fading particularly in the alkaline region was significant as the reagent layer was dried after color formation reaction.

COMPARATIVE EXAMPLE 5

(Effect of Water-soluble Polymeric Material Binder)

An ink composition for pH determination comprising the following ingredients was prepared in the same manner as that of Example 6, and applied onto a support by printing to produce a test device for pH determination.

|  | Parts by wt. |
| --- | --- |
| Sodium salt of Methyl Red | 0.07 |
| Bromothymol Blue | 0.30 |
| Ethyl cellulose (manufactured by Huckyless and marketed under the trade name N-50) | 5 |
| Microcrystalline cellulose (manufactured by Asahi Kasei Kogyo K.K., Japan, and marketed under the trade name ABICEL SF) | 36 |
| n-Butyl alcohol | 9 |
| Toluene | 50 |

The resulting test device was immersed in a body fluid to be tested. The time required for forming color was about one minute and a fading phenomenon was observed in 4–5 minutes.

EXAMPLE 8

An ink composition for detecting urobilinogen comprising the following ingredients was prepared by finely dividing and dispersing in a homomixer.

|  | Parts by wt. |
| --- | --- |
| p-Dimethylaminobenzaldehyde | 1.5 |
| Metaphosphoric acid | 5.0 |
| Polyoxyethylene sorbitan oleate | 1.0 |
| Isobutylene/maleic anhydride copolymer | 3.0 |
| n-Butanol | 54.5 |
| Microcrysalline cellulose | 35.0 |

The composition described above was sufficiently finely divided and dispersed in a homomixer, and then applied onto a white polystyrene sheet having a thickness of 250 μm by the screen printing process so that a tetragon having each side of 5 millimeters was formed. The screen plate used was of 100 mesh, and the sum of the thickness of a resist and a screen gauze was 130 μm.

The resulting printed matter was dried for 30 minutes at a temperature of 60° C. and cut into a strip form to produce a test device for detecting urobilinogen.

When the resulting test device was rapidly immersed in urine having the known concentration of urobilinogen, it rapidly formed a distinct color. This test device had high sensitivity and the formed color was extremely stable for a long period of time.

EXAMPLE 9

An ink composition for detecting occult blood comprising the following ingredients was prepared by finely dividing and dispersing in a homomixer.

|  | Parts by wt. |
| --- | --- |
| o-Tolidine | 1.0 |
| Oil Yellow | 0.05 |
| Cumenehydroperoxide | 2.5 |
| Polyoxyethylene sorbitan oleate | 1.0 |
| Isobutylene/maleic anhydride copolymer | 3.0 |
| n-Butanol | 57.5 |
| Microcrystalline cellulose | 35.0 |

The composition described above was sufficiently finely divided and dispersed in a homomixer, and then applied onto a white polystyrene sheet having a thickness of 250 μm by the screen printing process so that a tetragon having each side of 5 millimeters was formed. The screen plate used was of 100 mesh, and the sum of the thickness of a resist and a screen gauze was 130 μm.

The resulting printed matter was dried for 30 minutes at a temperature of 60° C. and then cut into a strip form to produce a test device for detecting occult blood.

When the resulting test device was rapidly immersed in urine having the known concentration of occult blood, it rapidly formed a distinct color. This test device had high sensitivity and the formed color was extremely stable for a long period of time.

EXAMPLE 10

The ink composition for detecting glucose described in Example 1, the ink composition for detecting protein described in Example 5, and the ink composition for pH determination described in Example 6 were used. The respective ink compositions were applied onto a white polystyrene sheet by printing so that a tetragon having each side of 5 millimeters was formed, thereby producing a test device capable of detecting glucose and protein present in a body fluid to be tested and capable of determining the pH thereof.

EXAMPLE 11

The ink composition for detecting glucose described in Example 1 and the ink composition for detecting protein described in Example 5 were used. The respective ink compositions were applied onto a white polystyrene sheet by printing so that a tetragon having each side of 5 millimeters was formed, thereby producing a test device capable of detecting glucose and protein present in a body fluid to be tested.

EXAMPLE 12

The ink composition for detecting glucose described in Example 1 and the ink composition for pH determination described in Example 6 were used. The respective ink compositions were applied onto a white polystyrene sheet by printing so that a tetragonal having each side of 5 millimeters was formed, thereby producing a test device capable of detecting glucose present in a body fluid to be tested, and capable of determining the pH thereof.

EXAMPLE 13

The ink composition for detecting glucose described in Example 1, the ink composition for detecting protein described in Example 5, the ink composition for pH determination described in Example 6, the ink composition for detecting urobilinogen described in Example 8, and the ink composition for detecting occult blood described in Example 9 were used. The respective ink compositions were applied onto a white polystyrene sheet by printing so that a tetragon having each side of 5 millimeters was formed, thereby producing a test device capable of detecting glucose, protein, urobilinogen and occult blood present in a body fluid to be tested and capable of determining the pH thereof.

EXAMPLE 14

A biaxially oriented polystyrene sheet was used as a support. An ink composition comprising the following ingredients was applied onto the polystyrene sheet by the silk screen printing process wherein a plate having 80 lines per inch was used. The resulting printed matter was dried for 30 minutes at a temperature of 60° C. to form stripe-shaped detection regions and water-retentive portions, each having a thickness of 160 μm and said stripe having a width of 2 mm. Thereafter, it was cut into an indicator strip having the form shown in FIG. 4.

An ink composition for forming water-retentive patterns comprised the following ingredients:

|  | Parts by wt. |
|---|---|
| Polyvinyl butyral resin (manufactured by Sekisui Kagaku K.K., Japan and marketed under the trade name BL-2) | 5 |
| Microcrystalline cellulose (manufactured by Asahi Kasei Kogyo K.K., Japan and marketed under the trade name ABICEL M-06) | 30 |
| Crosslinked carboxymethyl cellulose (manufactured by Asahi Kasei Kogyo K.K., Japan and marketed under the trade name AC-DI-SOL) | 10 |
| Butyl cellosolve | 55 |

The ink composition for detecting glucose described in Example 1, the ink composition for detecting protein described in Example 5 and the ink composition for pH determination described in Example 6 were used. These compositions were finely divided and dispersed in a homomixer to obtain an indicator strip.

The resulting indicator strip was immersed in urine and lifted up. The indicator strip was horizontally allowed to stand for a predetermined period of time (30 seconds), and thereafter the colored state was observed. The detection regions exhibited normal color formation and the contamination from other detection regions was not observed. Further. there was no color shading or mottle attendant upon the residue of droplets at the detection regions.

For comparison, the detection regions were formed as described above except that no water-retentive patterns were formed. The contamination due to the adjacent detection regions occurred and there was color shading or mottle attendant upon the residue of droplets at the detection regions. Thus, it was difficult to carry out color judgement.

Since the indicator strip of this example has water-retentive patterns at the periphery of the detection regions, the contamination due to the adjacent detection regions does not occur when a test is carried out. Since the droplets of a body fluid to be tested do not remain on the detection regions, there was no color shading or mottle. Accordingly, color judgement can be accurately carried out.

EXAMPLE 15

A test device for body fluids was produced in the same manner as that of Example 14 except that the following highly water-absorptive ink composition was used as the ink composition for forming water-retentive patterns. In this example, the ink composition was applied at a basis weight of 20 grams per square meter (on a dry basis) by the screen printing process.

|  | Parts by wt. |
|---|---|
| Sumika Gel SP 520 (available from Sumitomo Kagaku K.K., Japan) | 30 |
| Microcrystalline cellulose PH-06M (available from Asahi Kasei Kogyo K.K., Japan) | 10 |
| BYRON 300 (available from Toyo-bo K.K., Japan) | 9 |
|  | 9 |
| Cyclohexanone | 30 |
| Solvesso #150 | 21 |

BYRON 300 is a polyester resin, the exact composition of which is unknown and protected by trade secret. SOLVESSO 150 is a high boiling point-petroleum distillate, which is commercially available from Shell Oil.

What is claimed is:

1. A test device for body fluids comprising a support having printed or coated on a surface thereof at least one detection region, each detection region comprising a reagent composition selected from the group of reagent compositions consisting of:
   (a) a glucose detection reagent comprising a glucose oxidase, peroxidase, a peroxide oxidizable indicator, a glucose detection reagent binder and a color stabilizer which stabilizes said peroxide oxidizable indicator and a detectable product, said reagent being dissolved or dispersed in a nonaqueous solvent for the glucose detection reagent, said solvent excluding $C_1$ to $C_2$ alcohols;
   (b) a protein detection reagent comprising a pH indicator, a pH buffer, a protein-adsorptive ion exchanger, and a protein detection reagent binder, said reagent being dissolved or dispersed in a nonaqueous solvent for the protein detection reagent; and
   (c) a pH determination reagent comprising a pH indicator, and a pH determination reagent binder, said reagent being dissolved or dispersed in a non-aqueous solvent for the pH determination reagent; and
   at least one water-retentive pattern portion formed on said surface of said support between and coplanar with each of said detection regions such that adjacent detection regions are separated by at least one water-retentive pattern portion;
   wherein said support is nonadsorptive, the water retentive pattern portions have a capacity of absorbing water of at least 10 times their own weight, and spaces are provided on said support between each of said detection regions and each of said water-retentive pattern portions.

2. The test device as claimed in claim 1, wherein the oxidizable indicator in the glucose detection reagent comprises either a chromogen or a chromogen and a coupling agent.

3. The test device as claimed in claim 1, wherein the color stabilizer in the glucose detection reagent is a tocopherol or a glycerol ester.

4. The test device as claimed in claim 1, wherein the protein-adsorptive ion exchanger in the protein detection reagent is an acidic cation exchanger having as a functional group a carboxyl group, and the protein detection composition binder is a maleic acid ester copolymer.

5. The test device as claimed in claim 1, wherein the pH determination reagent binder comprises hydroxy ethylcellulose or a polyvinyl pyrrolidone, both of which are water-soluble polymers which do not impede color formation of the pH indicator, and a urethane resin or a polyvinyl butyral resin which is a water-insoluble polymer capable of effectively preventing the elution of the pH determination reagent into an applied body fluid.

* * * * *